(12) United States Patent
Berry et al.

(10) Patent No.: US 11,471,356 B2
(45) Date of Patent: Oct. 18, 2022

(54) SHELF FOR DENTAL DELIVERY SYSTEM

(71) Applicant: A-dec, Inc., Newberg, OR (US)

(72) Inventors: Patrick W. Berry, Vancouver, WA (US); Joseph Van Domelen, Hillsboro, OR (US); Rebekah Slyter, Newberg, OR (US)

(73) Assignee: A-dec, Inc., Newberg, OR (US)

( * ) Notice: Subject to any disclaimer, the term of this patent is extended or adjusted under 35 U.S.C. 154(b) by 835 days.

(21) Appl. No.: 16/387,441

(22) Filed: Apr. 17, 2019

(65) Prior Publication Data

US 2020/0330312 A1    Oct. 22, 2020

(51) Int. Cl.
*A61G 15/14*    (2006.01)
*A61C 1/00*    (2006.01)
*A61B 50/20*    (2016.01)

(52) U.S. Cl.
CPC .............. *A61G 15/14* (2013.01); *A61B 50/20* (2016.02); *A61C 1/0061* (2013.01)

(58) Field of Classification Search
CPC ........ A61B 50/20; A61G 15/14; A61G 15/16; A61G 15/18; A61C 1/0061
See application file for complete search history.

(56) References Cited

U.S. PATENT DOCUMENTS

| | | | | |
|---|---|---|---|---|
| 3,346,957 A | * | 10/1967 | Maurer | A61C 1/0007 433/79 |
| 3,691,634 A | * | 9/1972 | Buchtel | A61G 15/14 433/79 |
| 3,872,593 A | * | 3/1975 | Thornton, Jr. | A61G 15/14 433/101 |
| 3,949,480 A | * | 4/1976 | Page | A61G 15/16 433/27 |
| 3,986,263 A | * | 10/1976 | Borgelt | A61G 15/16 433/33 |
| 4,138,815 A | * | 2/1979 | Williams | A61G 15/14 433/77 |
| 4,209,908 A | | 7/1980 | Fleer | |
| 4,217,009 A | * | 8/1980 | Suter | A61G 15/16 433/79 |

(Continued)

FOREIGN PATENT DOCUMENTS

| | | | |
|---|---|---|---|
| DE | 29507560 U1 * | 8/1996 | ............. A61G 15/14 |
| DE | 102008023842 A1 * | 11/2009 | ............. A61G 15/18 |

(Continued)

OTHER PUBLICATIONS

International Search Report and Written Opinion for PCT/US2020/028571, dated Jul. 29, 2020.

*Primary Examiner* — Stanton L Krycinski
(74) *Attorney, Agent, or Firm* — Klarquist Sparkman. LLP

(57) ABSTRACT

A shelf for a dental delivery system comprises a shelf member and device mounting locations on the shelf member. The shelf member is shaped to fit within a dental delivery system housing. The shelf member is movable between at least a closed position and an open position. The device mounting locations define locations devices can be coupled. According to another implementation, a dental delivery system comprising a housing defining an interior, at least one connection extending from the housing to a dental handpiece holding area, a removable cover and a shelf member movable between at least open and closed positions is described.

22 Claims, 20 Drawing Sheets

(56) References Cited

U.S. PATENT DOCUMENTS

| | | | | |
|---|---|---|---|---|
| 4,359,316 A * | 11/1982 | Kummel | ............... | A61G 15/16 433/79 |
| 4,571,182 A * | 2/1986 | Beier | ............... | A61G 15/14 433/79 |
| 4,952,146 A * | 8/1990 | Doty | ............... | A61G 15/14 433/77 |
| 5,211,558 A * | 5/1993 | Bailey | ............... | A61C 1/0053 433/77 |
| 5,399,007 A * | 3/1995 | Marconet | ............... | A61B 50/13 312/249.8 |
| 5,435,448 A * | 7/1995 | Kempen | ............... | A61B 50/20 206/370 |
| 5,784,251 A | 7/1998 | Miller et al. | | |
| 6,692,253 B2 * | 2/2004 | Brockway | ............... | A61G 15/16 433/77 |
| 6,705,474 B1 * | 3/2004 | Buczek | ............... | A61B 50/20 211/70.6 |
| 6,736,360 B1 * | 5/2004 | Buczek | ............... | A61B 50/10 248/278.1 |
| 7,229,285 B2 * | 6/2007 | Behr | ............... | A61B 50/20 433/77 |
| 7,581,951 B2 * | 9/2009 | Lehmann | ............... | A61G 15/16 433/79 |
| 7,748,529 B2 * | 7/2010 | Foreman | ............... | A61B 50/34 220/23.88 |
| 8,056,720 B2 * | 11/2011 | Hawkes | ............... | A61B 50/31 206/439 |
| 8,096,807 B2 * | 1/2012 | Benfield | ............... | A61C 17/06 433/92 |
| 8,104,614 B2 * | 1/2012 | Pinal | ............... | A61B 50/00 206/370 |
| 8,438,979 B2 * | 5/2013 | Song | ............... | A61B 50/15 108/50.01 |
| 8,568,391 B2 * | 10/2013 | Kerns | ............... | B65D 83/00 606/1 |
| 9,072,543 B2 * | 7/2015 | Miller | ............... | A61B 17/3472 |
| 10,835,339 B2 * | 11/2020 | Krensky | ............ | A61B 50/3001 |
| 10,987,205 B2 * | 4/2021 | DeBord | ............... | A61B 90/90 |
| 11,039,971 B2 * | 6/2021 | Berry | ............... | A61G 15/02 |
| 11,185,389 B2 * | 11/2021 | Williams | ............ | A61C 1/0061 |
| 11,273,231 B2 * | 3/2022 | Jackson | ............... | A61B 50/30 |
| 2003/0073053 A1 | 4/2003 | Brockway et al. | | |
| 2004/0144673 A1 * | 7/2004 | Buczek | ............... | A61B 50/13 206/438 |
| 2007/0119737 A1 * | 5/2007 | Wood | ............... | A61B 50/31 206/363 |
| 2008/0040885 A1 | 2/2008 | Daoud et al. | | |
| 2008/0166682 A1 * | 7/2008 | Bjorn | ............... | A61B 50/33 433/77 |
| 2008/0182224 A1 * | 7/2008 | Ahearn | ............... | A61G 15/16 433/77 |
| 2010/0190131 A1 | 7/2010 | Benfield et al. | | |
| 2013/0001180 A1 * | 1/2013 | Stout | ............... | A61B 50/20 211/85.13 |
| 2020/0107912 A1 * | 4/2020 | Schlueter | ............ | A61B 50/20 |
| 2021/0085415 A1 * | 3/2021 | Stalter | ............ | A61B 8/4405 |

FOREIGN PATENT DOCUMENTS

| | | | | |
|---|---|---|---|---|
| DE | 102019105312 A1 * | 6/2020 | ............ | A61C 3/025 |
| FR | 2032548 A5 * | 11/1970 | | |
| FR | 2041910 A5 * | 2/1971 | | |
| FR | 2253495 A1 * | 7/1975 | | |
| FR | 2592565 A1 * | 7/1987 | | |
| FR | 2683665 A1 * | 5/1993 | ............ | A61G 15/14 |
| GB | 1492461 | 11/1977 | | |
| GB | 1501365 | 2/1978 | | |
| KR | 20120085676 A * | 8/2012 | | |

* cited by examiner

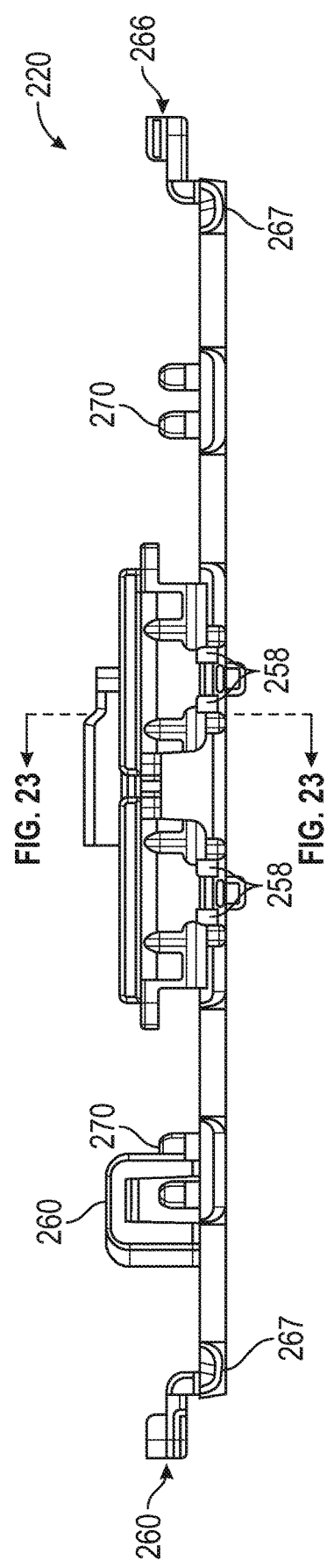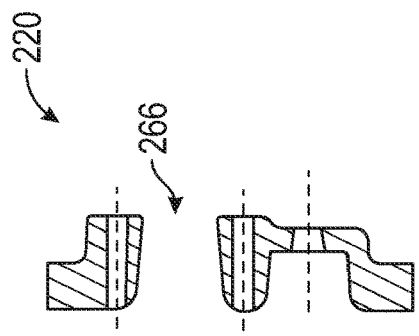

SHELF FOR DENTAL DELIVERY SYSTEM

BACKGROUND

Dental delivery systems are used during dental procedures to arrange dental instruments, referred to herein as handpieces, at locations convenient to the practitioner. Dental handpieces have an array of operating requirements, including supplies of electrical and pneumatic power, suction, water and data. Typically, handpieces are connected to the dental delivery system by conduits, tubing, cables and the like. With the multiple handpieces that are typically required by the practitioner, there are a great number of routings and connections among the conduits, tubing and cables in the delivery system housing.

As a result, if one of the handpieces needs to be serviced or replaced, the task can be difficult because tracing the connections to the affected handpiece is complicated. It may be necessary to move connections for other unaffected handpieces in order to isolate the affected handpiece. There is also a possibility of inadvertently disrupting a connection or otherwise negatively impacting the operation of the delivery device because of the difficulties in accessing only the affected connections.

SUMMARY

Described below are implementations of a shelf for a delivery system that address problems with conventional delivery systems.

According to one implementation, a shelf for a dental delivery system comprises a shelf member shaped to fit within a dental delivery system housing that is movable between at least a closed position and an open position and device mounting locations on the shelf member at which devices can be coupled.

The shelf member can be configured to be pivotably movable relative to the delivery device housing. The shelf member can comprise at least one pivot.

The device mounting locations can comprise slots formed in the shelf member.

The shelf member in the closed position can be shaped to define an area of the housing below the shelf member that is separated from an area above the shelf member.

The shelf member further can comprise at least one arched area projecting outwardly and defining an internal routing space for cables or tubing.

The shelf member can comprise at least one arched area projecting outwardly and defining a recess therein through which an equipment arm can extend.

The shelf member can comprise multiple defined locations for connections extending to handpieces. The shelf member can comprise channel portions sized to receive at least one electrical cord or tubing.

The shelf member can comprise at least one retainer member to positively retain the shelf member in the closed position. The shelf member can comprise a lift tab by which the shelf member can be moved between the open and closed positions.

The shelf member can be configured to provide mounting positions for at least one of a camera module, a hybrid air/electric motor module, a USB hub, a dual electric motor module, a scaler module and a curing light module.

The shelf member can comprise multiple strain relief mounts, each strain relief mount being configured to receive a corresponding strain relief portion of a handpiece to be connected to the delivery system to aid in preventing damage to the handpiece conduit when pulled or tugged.

According to another implementation, a dental delivery system comprises a housing defining an interior, at least one connection extending from the housing to a dental handpiece holding area, the connection being connectable to a dental handpiece, a cover fitted to the housing, wherein the cover is removable to access the interior, and a shelf member sized to fit within the interior and being movable between at least open and closed positions.

The at least one connection can comprise a conduit for fluid, electrical power or data, and wherein the conduit is associated with at least one device mounted to the shelf member.

The cover can be pivotably connected to the housing, such that when the cover is pivoted to an open position, the shelf member can be pivoted from the closed position to the open position.

The shelf member and the housing can comprise a retainer arrangement for retaining the shelf member in a closed position relative to the housing.

The shelf member in the closed position can define a lower area of the housing at a level below the shelf member and an upper area of the housing above the shelf member. There can be at least one fluid conduit is routed through a lower area of the housing.

The foregoing and other objects, features, and advantages of the disclosed technology will become more apparent from the following detailed description, which proceeds with reference to the accompanying figures.

BRIEF DESCRIPTION OF THE DRAWINGS

FIGS. 19-21 are top plan, bottom plan and front elevation views, respectively, of the shelf member of FIG. 11 shown in isolation.

FIG. 22 is a section view taken along the line A-A in FIG. 21.

DETAILED DESCRIPTION

Described below are implementations of a shelf fitted to an interior of a dental delivery system (also referred to herein as a dental unit or a control head) that provides access for mounting various components and can be moved to provide access to other areas of the interior.

Figure 1:
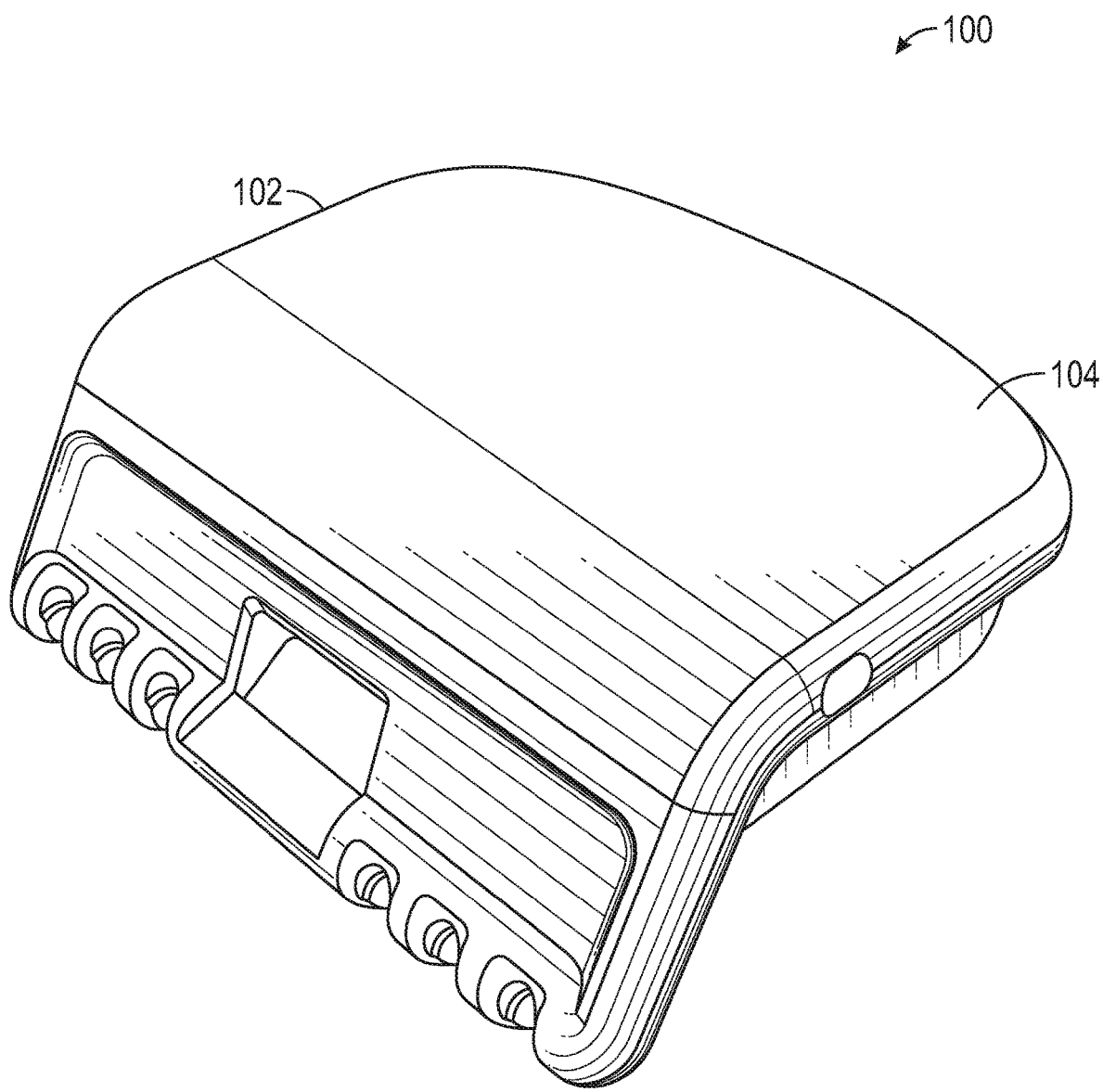
FIG. 1 is a perspective view of a dental delivery system housing, shown in isolation.

FIG. 1 is a perspective view of a housing 102 for a representative dental delivery system 100, which is shown in isolation and with its cover 104 in place.

Figure 2:
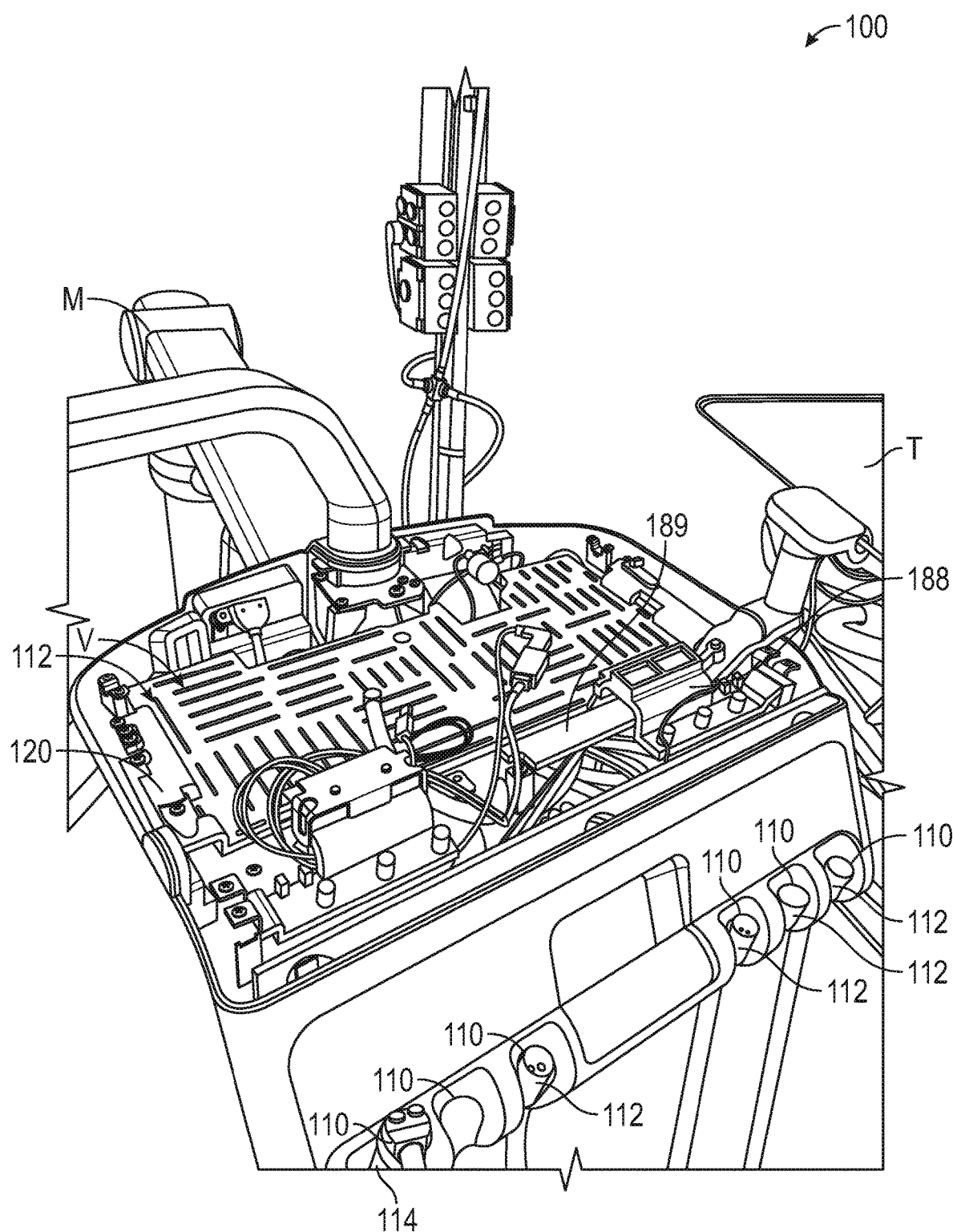
FIG. 2 is a perspective view of the dental delivery system of FIG. 1, shown in an operating environment and with its cover removed.

FIG. 2 is a perspective view of the dental delivery system 100 with its cover 104 removed and as configured for use in a dental operatory environment. The delivery system 100 is supported by a movable arm M, and supports additional equipment, including, e.g., a tray T and a control device C (FIG. 3) that includes a display. The delivery system 100 as shown has six holding spaces 110 for handpieces, five of which are shown occupied (including four by coupling elements 112 and one by a dental air/water syringe 114) at the ends of respective conduits for receiving air, water, suction, electrical power, data, etc., via connections within and/or near the housing 102. The coupling elements 112 are configured to provide connections for other handpieces (in addition to the dental syringe 114), as described generally below.

Figure 3:
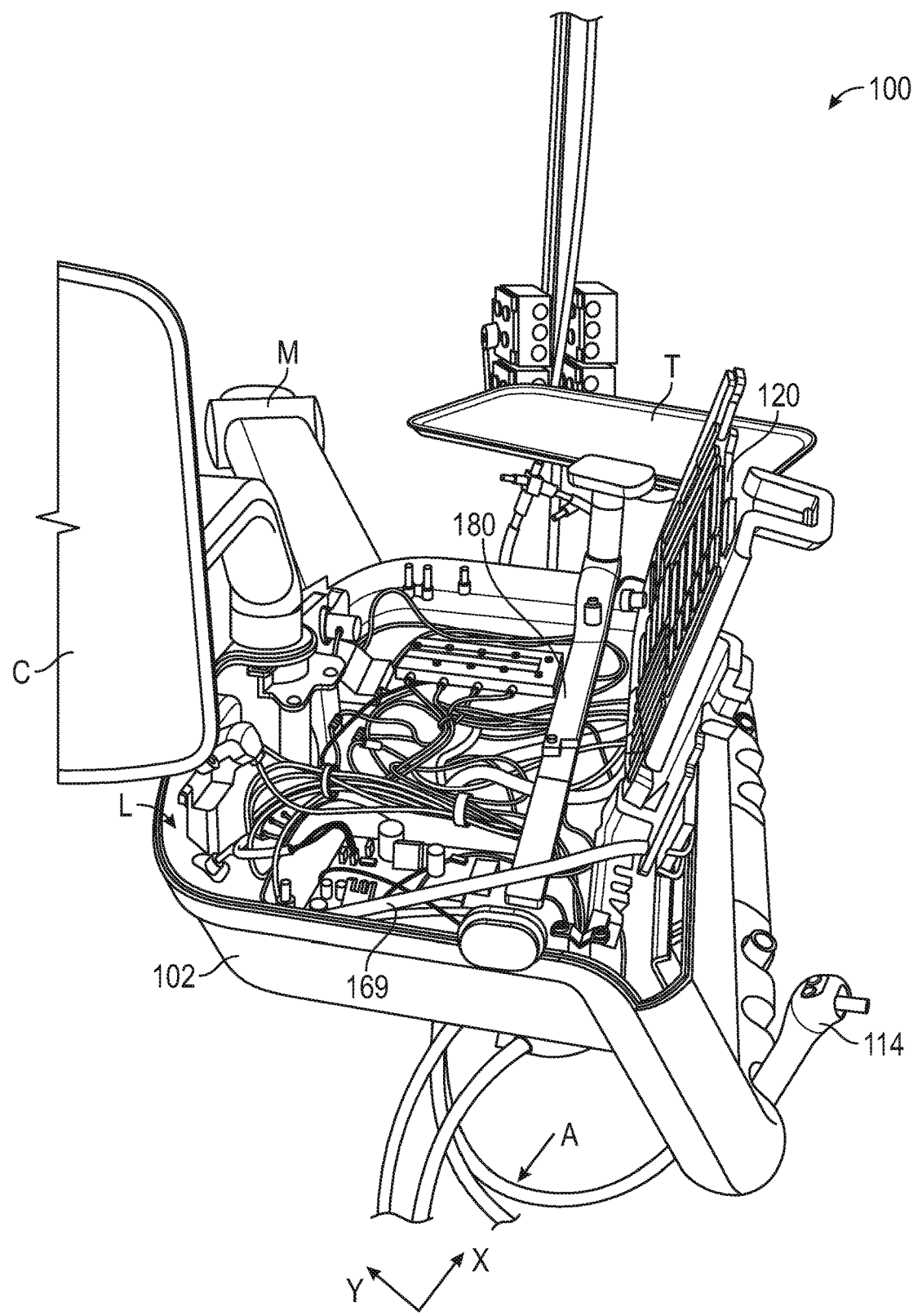
FIG. 3 is another perspective view of the dental delivery system of FIG. 2, shown with a shelf member pivoted to an open position to provide additional access.

Referring to FIGS. 2 and 3, the housing 102 is fitted with a shelf member 120 which can be moved between at least a closed position (FIG. 2) and an open position (FIG. 3). In the illustrated implementation, the shelf member 120 is configured to move between the closed and open positions by pivoting about a pivot axis A, which is defined to be parallel to an X axis. Thus, the X axis extends in a direction from the left side to the right side of the housing, whereas the Y axis extends in a direction from the front to the rear of the housing. Other arrangements to provide for the shelf to be movable between the closed and open positions are also possible.

The shelf member 120 provides mounting locations for various devices on at least its upper surface (and in some cases, also its lower surface), and is spaced above areas of the housing that are well occupied as shown, including by conduits, cables, wiring, other devices, etc. (FIG. 3). The shelf thus also helps to organize the space within the housing by defining different areas, including at least an upper area U above the shelf member 120 when it is in the closed position and a lower area L of the housing below the shelf member 120. In this way, the different areas can be used for different purposes. For example, the upper area U can be used to house devices and connections that require more frequent attention and/or or more frequently accessed in the field, whereas the lower area L can be used for basic devices and connections that area less likely to need attention. Additionally, the lower area can be used for mounting standard components or devices that are typically installed during initial assembly, while the upper area can be used for mounting optional devices that are added, removed or upgraded at any time during the life of the dental delivery system. In some implementations, e.g., access to the lower area L could be controlled (e.g., with a lock).

By physically and logically separating different areas from each other, the shelf increases utilization of space with the housing 102. In addition, the various devices and their connections can be laid out in more orderly ways, which leads to completing tasks such as tending to or swapping devices more quickly and easily and with greater assurance against inadvertently disturbing other devices and connections and/or making incorrect connections. Further, conduit and cable lengths can be kept shorter than in other arrangements that are not "stacked" to minimize footprint.

Figure 4:
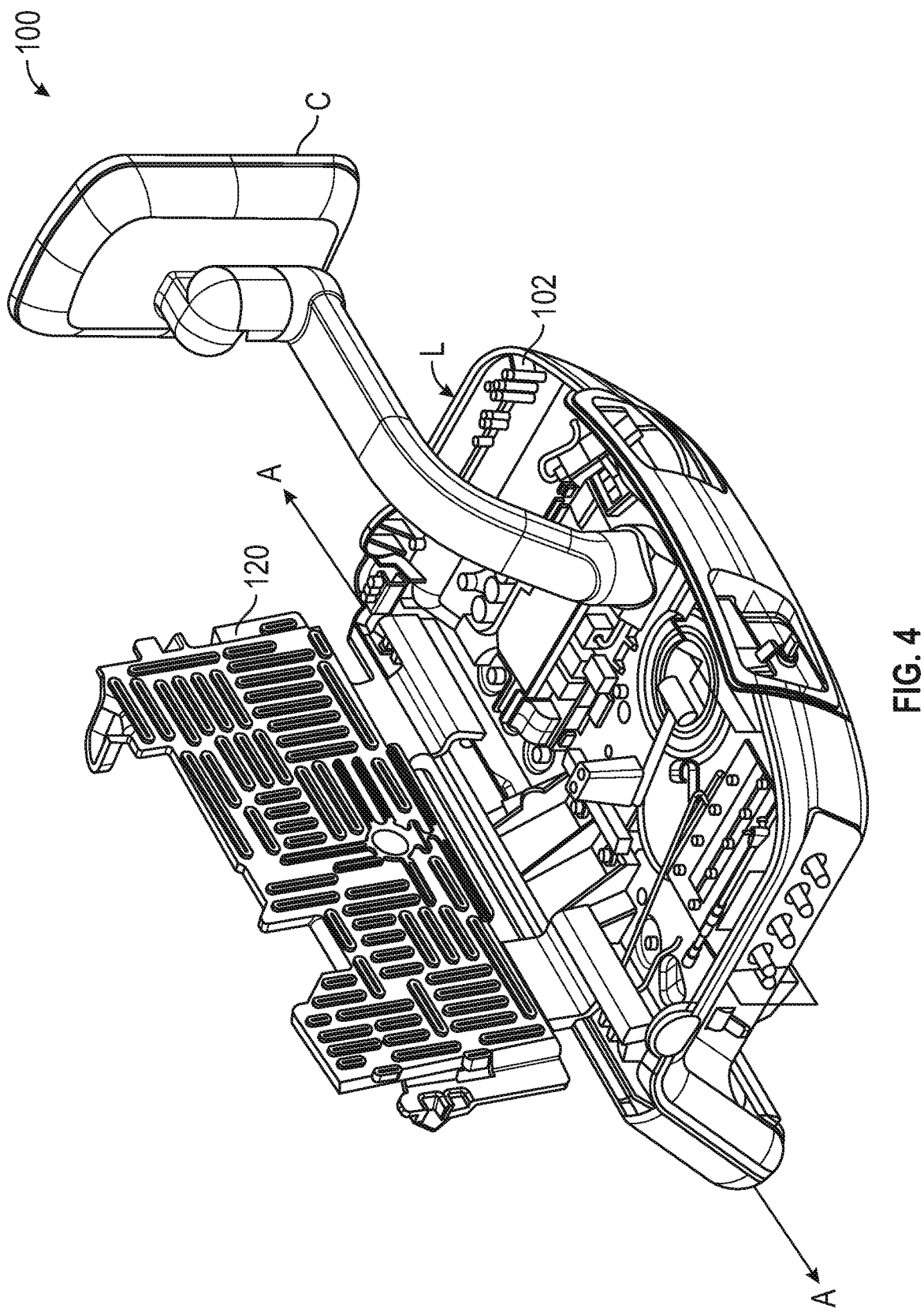
FIG. 4 is a perspective view of the dental delivery system from another angle with the shelf member pivoted to the open position.
Figure 5:
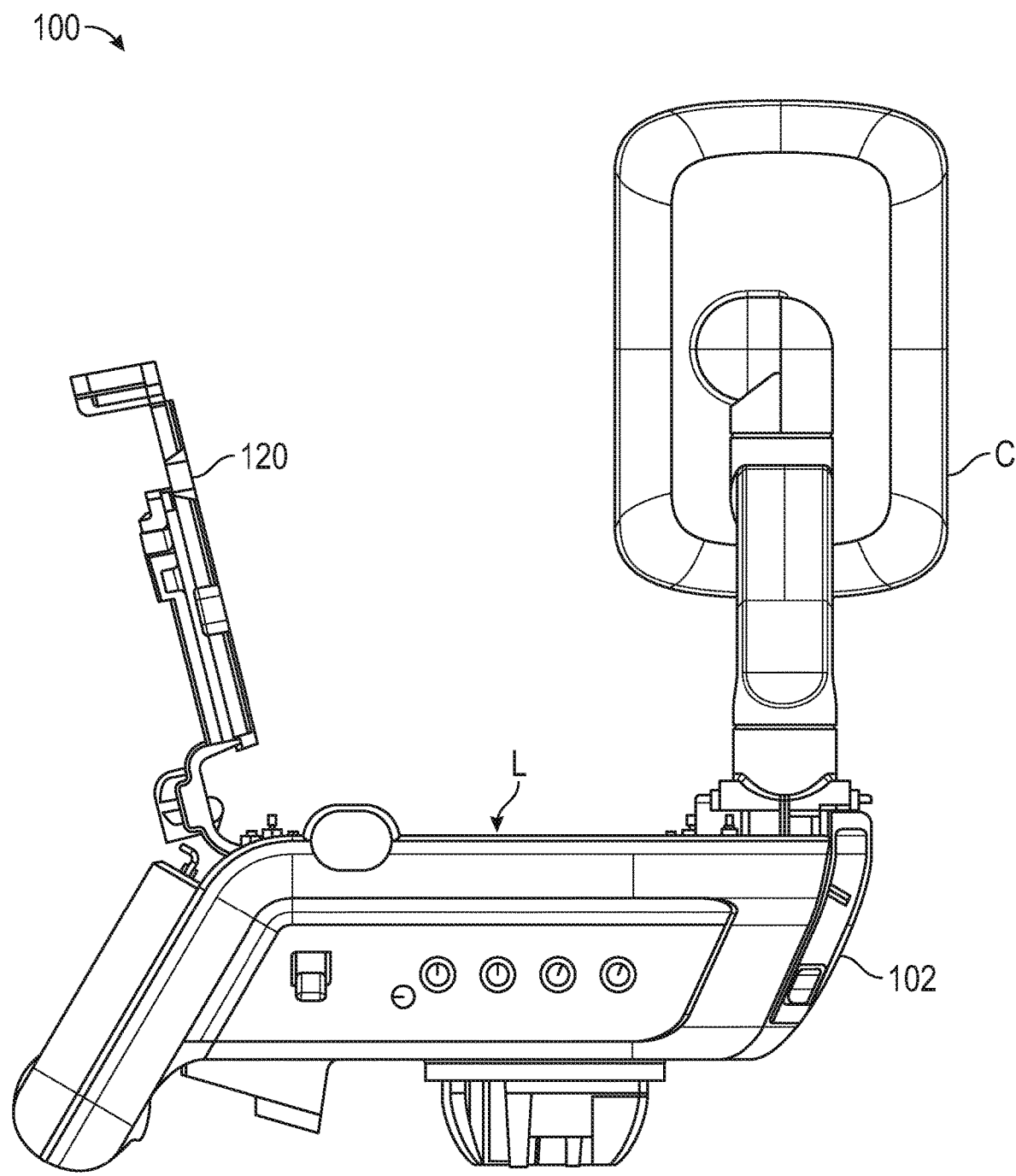
FIG. 5 is a side elevation view of the dental delivery system with the shelf member pivoted to the open position.

FIG. 4 is an additional perspective view showing the housing 102 with the shelf member 120 in the open position from another angle. FIG. 5 is a side elevation view showing the shelf member in a fully open position.

FIGS. 12-15 are perspective, top plan, bottom plan and front elevation views, respectively, of the shelf member 120. As shown, the shelf member 120 has pivots 158 arranged on the pivot axis A and shaped to be received in corresponding areas at opposite sides of the housing 102. The shelf member 120 can be rotated or pivoted about the pivots 158 between at least fully open and closed positions.

There is a lift tab 160 that projects away from an upper surface T of the shelf member 120 to assist a user in urging moving the shelf member between closed and open positions. The upper surface includes an array of X direction slots, such as at 162, and Y direction slots, such as 164, for coupling devices, etc. to the shelf member 120. It would of course be possible to provide slots extending in other directions, openings of round, square or other shapes, or projections, instead of or in addition to the slots 162, 164.

Figure 16:
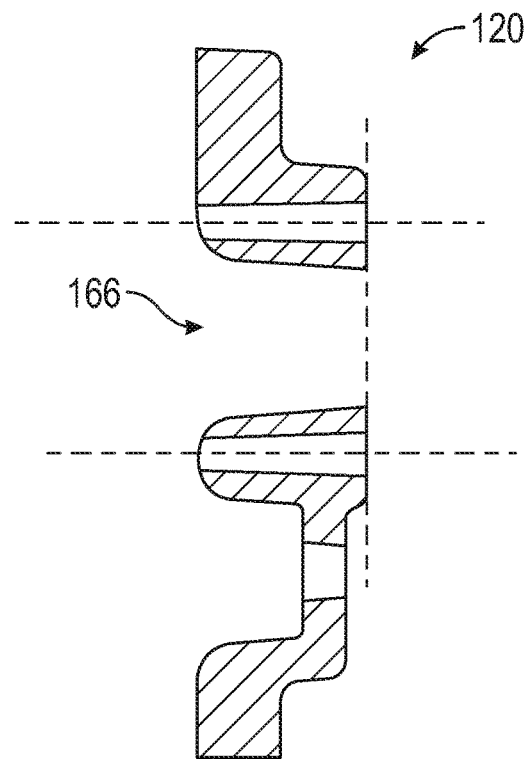
FIG. 16 is a section view taken along the line A-A in FIG. 13.

Along the side edges, there are retaining device areas 166 for mounting a retaining device or other similar retaining device designed to retain the shelf member 120 in a desired position, such as the closed position. In one implementation, the retaining device 169 includes a boss with a ball mounted in the housing 102 and a retaining member 169 shaped to receive the ball (FIG. 10) to secure the shelf member 120 in the closed position. FIG. 16 is a section view taken at the line A-A in FIG. 13 and showing the structure of the shelf 120 in the retaining device area 166 in more detail.

Figure 6:
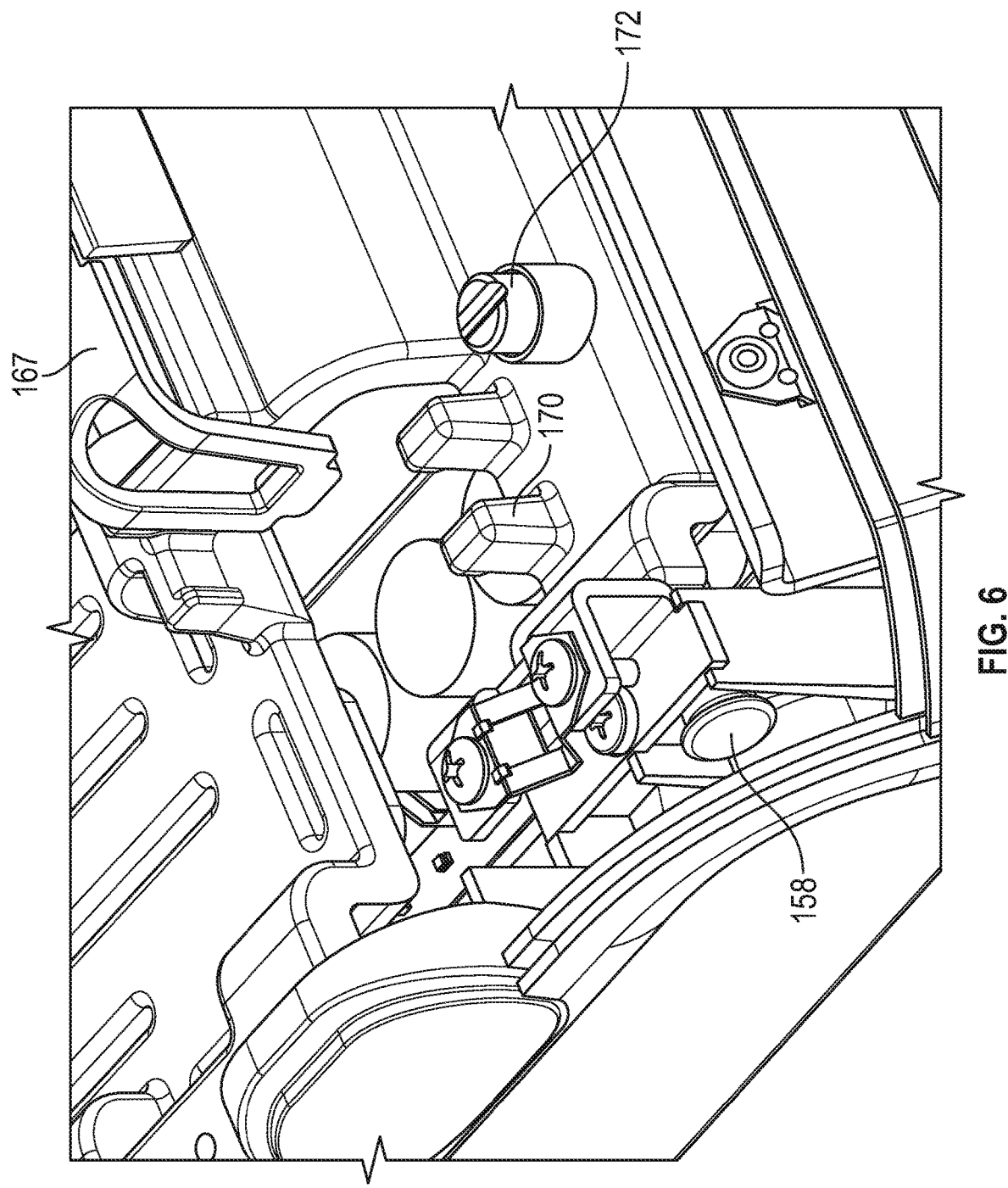
FIG. 6 is a magnified perspective view of a portion of the dental delivery system.

Also along the side edges, there are formed features 167 for guiding and securing electrical wires running between the lower and upper areas. The features 167 can include channel portions and one or more eyelets for securing wires in the channel portions with cable ties. FIG. 6 is a magnified perspective view of a portion of the shelf member 120 showing the features 167 and an added retainer.

The shelf member 120 can have a lanyard mount 168 for mounting a lanyard L (FIG. 3) that serves to prevent the shelf member from being over-rotated. A pair of projections 170 can be provided for routing tubing, cables, etc., especially in the Y direction. Conventional cable ties can be used for securing such tubing and/or cables in the area of the projections 170 (as well as elsewhere on the shelf member 120, such as in any of the exposed slots 162, 164).

Figure 17:
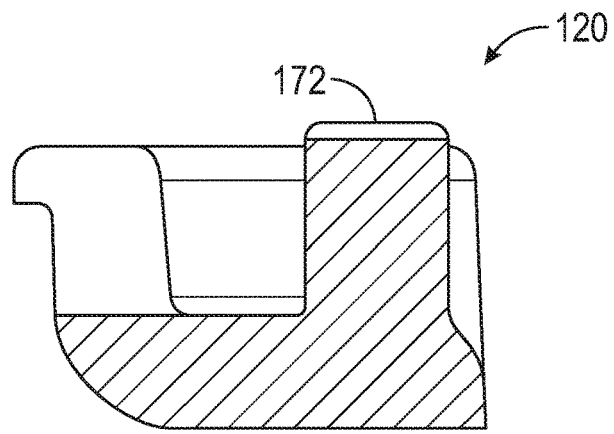
FIG. 17 is a section view taken along the line B-B in FIG. 15.

The shelf member. 120 can have projections 172, such as one for each of the handpiece positions (numbered 1-6 as shown), to secure a strain relief for a handpiece (not shown) connected at the corresponding location. FIG. 17 is a section view taken along the line 13-B in FIG. 15 and showing one of the projections 172 in more detail. In the implementation depicted, a strain relief cord can be secured to the projection 172 by capturing the strain relief cord between the projection 172 and a tightly fitting cylindrical collar (not shown) slid over the projection 172. Other alternatives for securing a strain relief are possible (e.g., a zip tie could be used).

Figure 18:
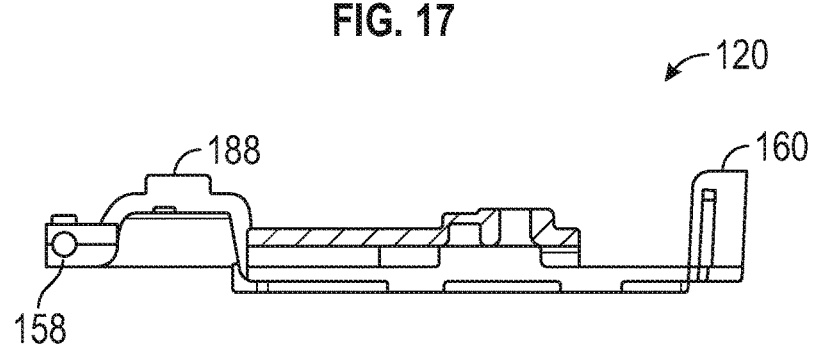
FIG. 18 is a section view taken along the line C-C in FIG. 15.

The shelf member 120 can have one or more arched sections 188 that project away from the plane of the shelf member 120 to define "bumped" routing spaces for routing cables, tubing, etc. In the shelf member 120, the arched sections are located relatively close to the pivot axis A. FIG. 18 is a section view taken along the line C-C in FIG. 15 and showing the arched section 188 and the routing space it defines for one side of the shelf member 120. In FIG. 2, the arched section 188 provides clearance for an equipment arm, such as a tray arm 189.

The shelf member 120 can be shaped to have a large clearance 186 as shown to provide space for tubing and cables to crisscross each other as they extend from left to right (and vice versa). In addition, the clearance 186 can provide space a portion of a device, such as a USB hub 138 (FIG. 10) to overhang the shelf member 120, as is described in more detail below.

The shelf member 120 can have an opening 190 for providing access to a friction adjustment in the housing 102 for adjusting the amount of friction applied in repositioning the delivery system 100.

Figure 7:
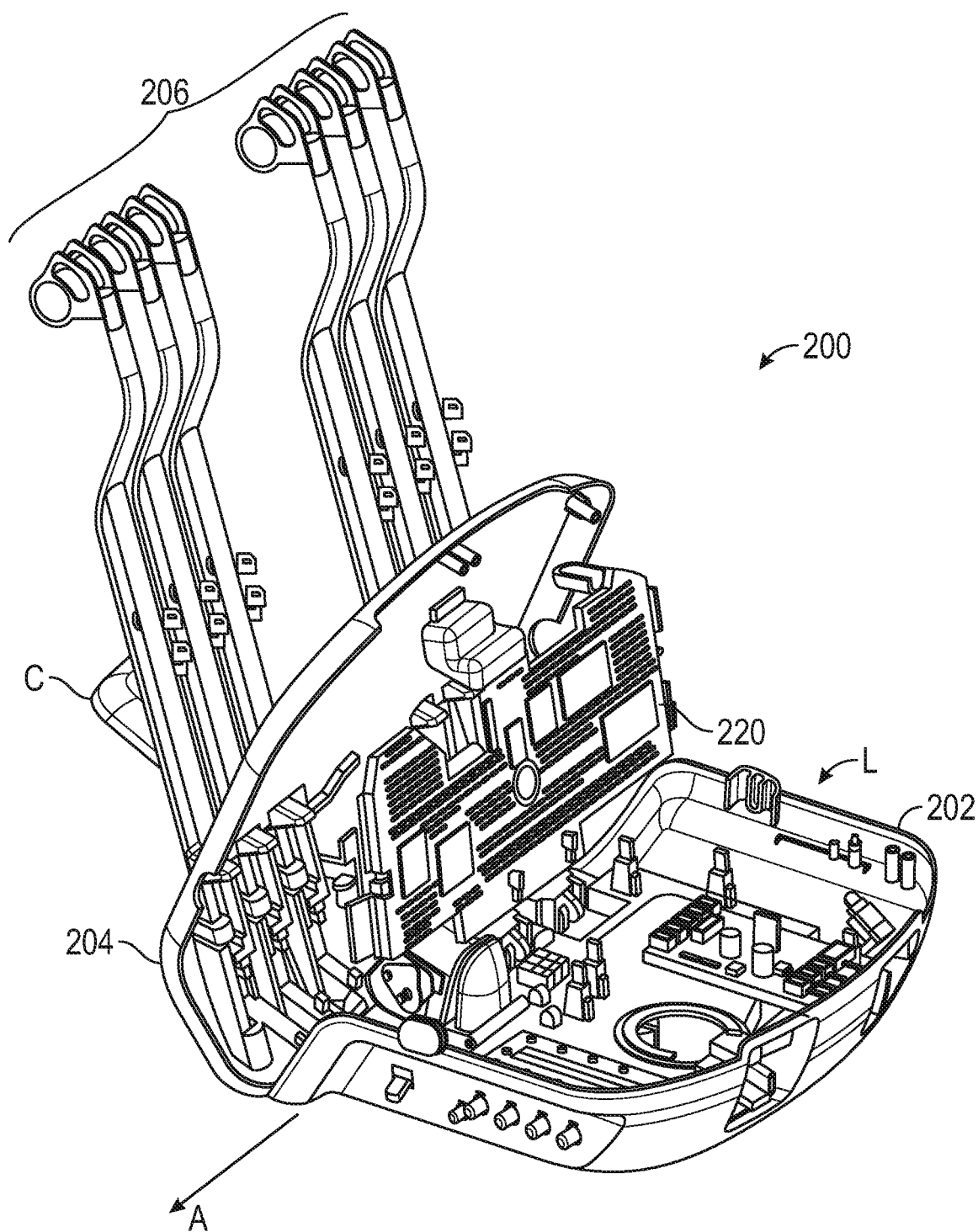
FIG. 7 is a perspective view of an alternative dental delivery system, shown with its shelf member and cover pivoted to open positions.
Figure 8:
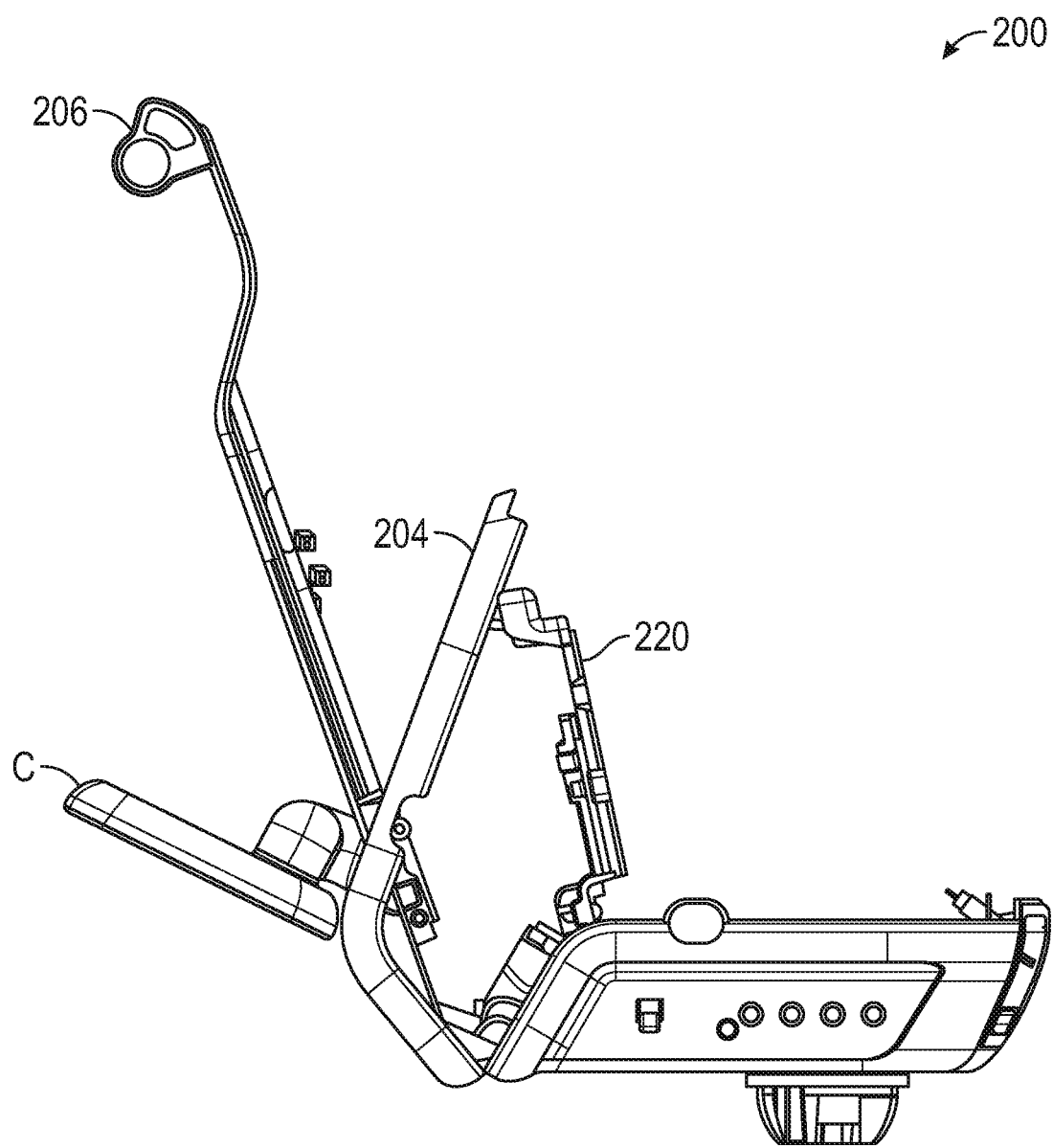
FIG. 8 is a side elevation view of the dental delivery system of FIG. 7.
Figure 19:
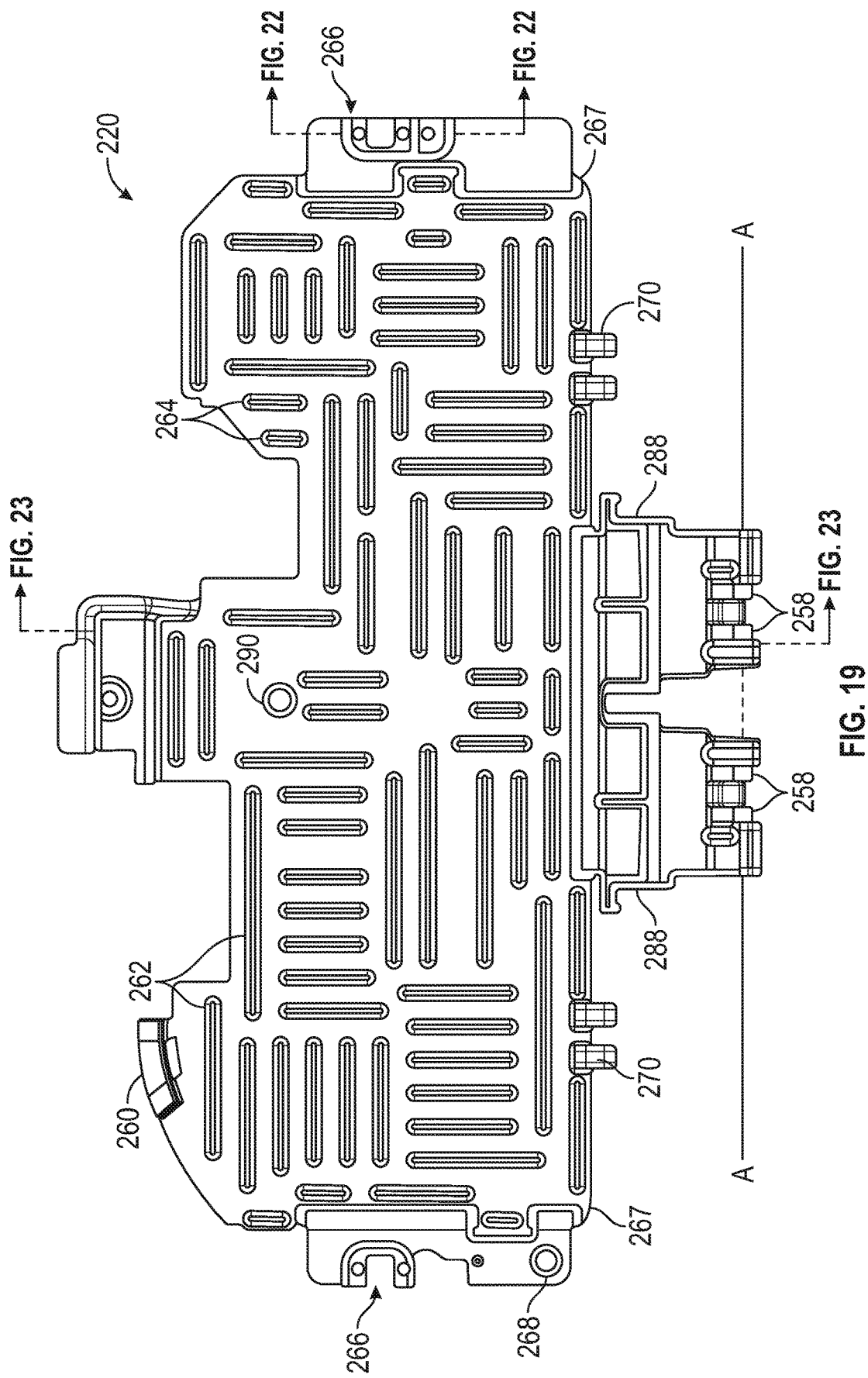
Figure 20:
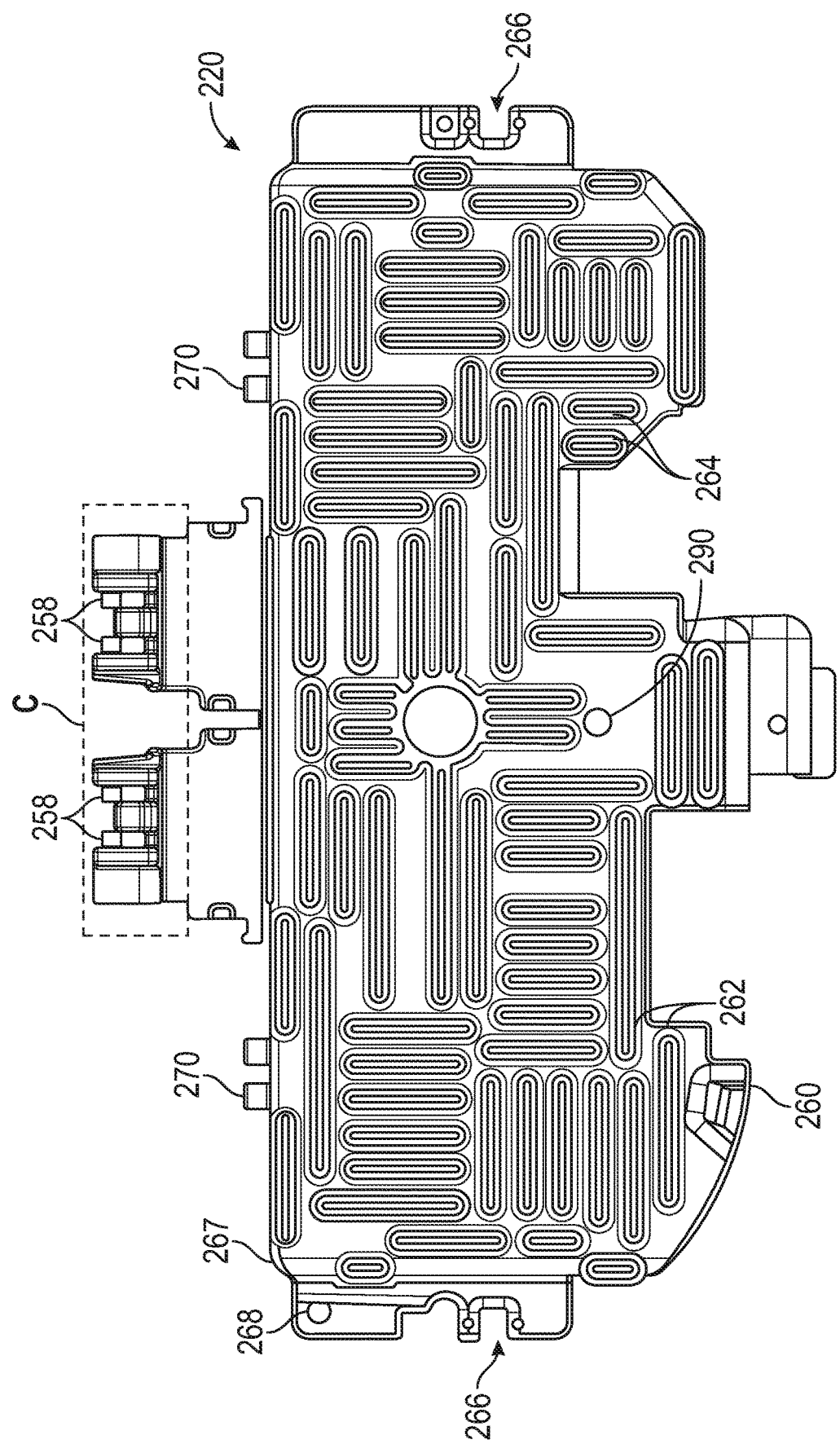
Figure 23:
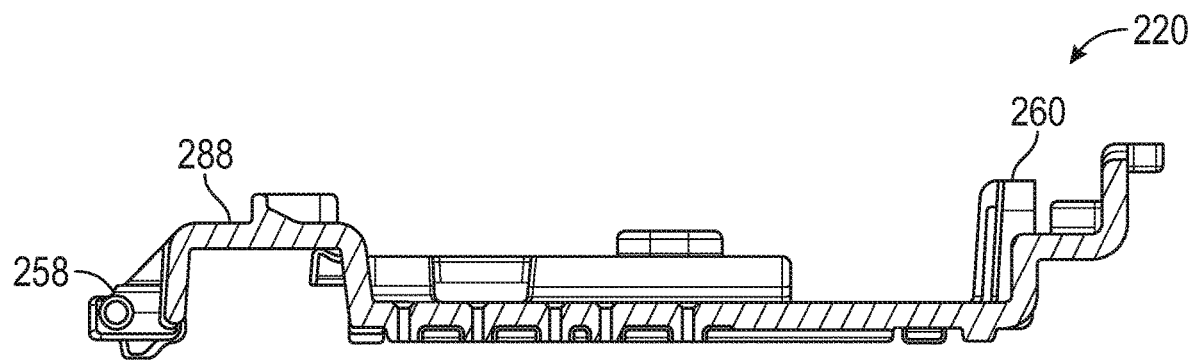
FIG. 23 is a section view taken along the line B-B in FIG. 21.
Figure 24:
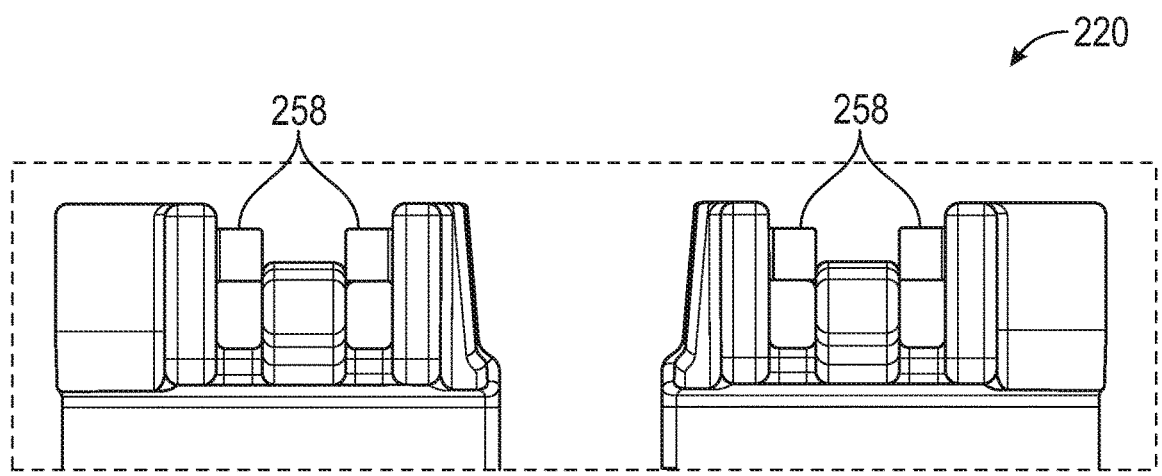
FIG. 24 is a magnified detail view of the area C in FIG. 20.

FIGS. 7 and 8 are perspective and side elevation views, respectively, of another representative delivery system 200 showing its hinged cover 204 and shelf member 220 rotated to open positions to provide access to the lower area U of the housing 202. The delivery system 200 as shown is referred to as a continental style delivery system and has multiple whip arms 206 that guide conduits for handpieces (not shown). FIGS. 19-21 are top plan, bottom plan and front elevation views, respectively, of the shelf member 200. FIGS. 22 and 23 are section views taken from FIGS. 19 and 21, and FIG. 24 is a detail view taken from FIG. 20. In general, components of the delivery system 200 are numbered with the same reference number plus 100 as the same or similar components in the delivery system 100.

Figure 9:
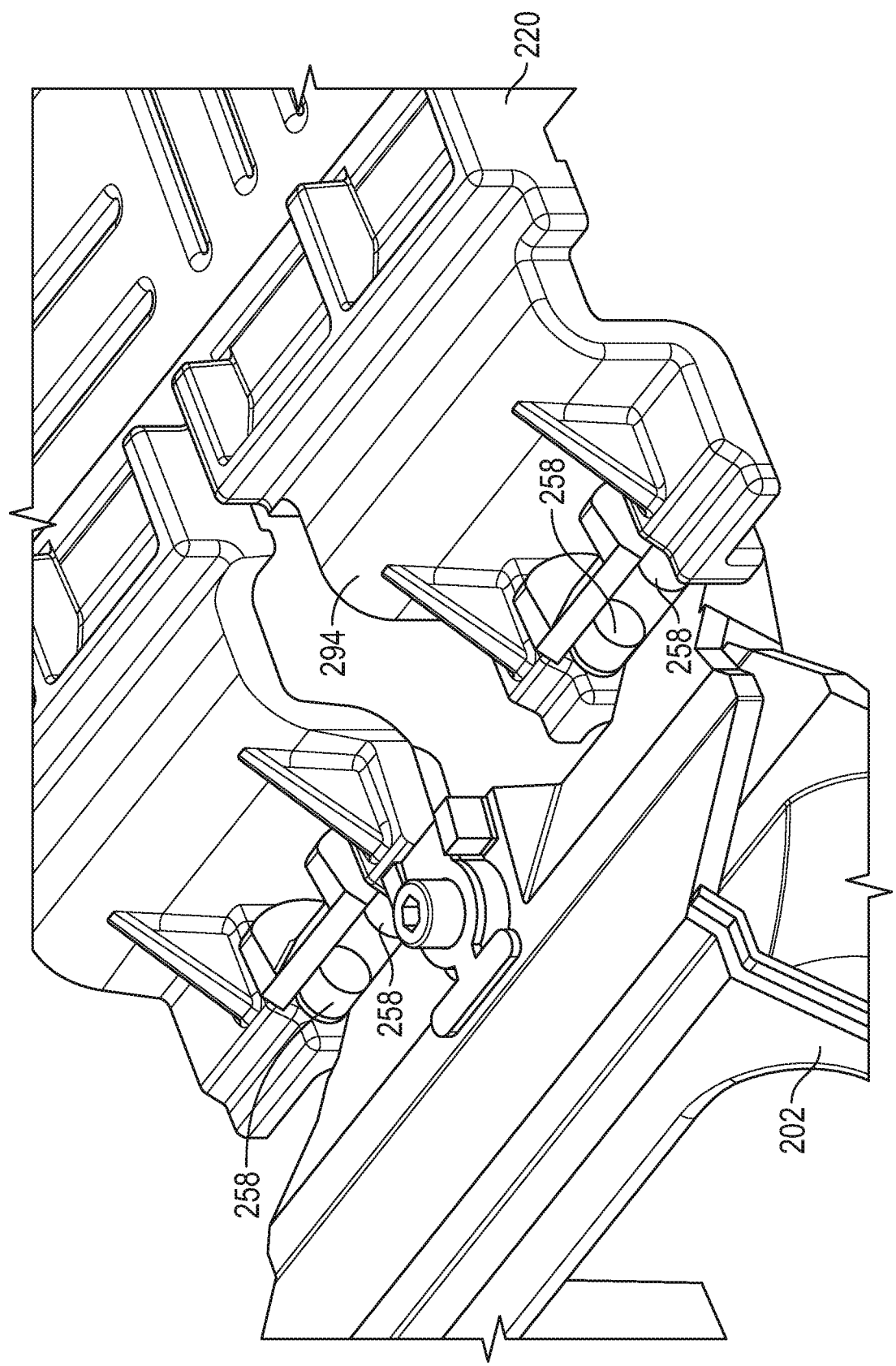
FIG. 9 is a magnified perspective view of a portion of the dental delivery system of FIG. 7.

As shown in FIGS. 7 and 8, the cover 204 (including the whip arms 206 and the control device C) is designed to be pivoted to open the housing 202, and the shelf member 220 can then be moved to allow access to the lower area L, such as by rotating or pivoting the shelf member 220 to the position shown. As shown in FIG. 9, there are two pairs of pivots 258 in the shelf member 220, and they are spaced more closely together than in the shelf member 120. FIG. 9 is a partial perspective view at a magnified scale showing the pivots 258. As also shown in FIG. 9, an angled stop surface 294 can be provided to stop the shelf member 220 from over-rotation.

Figure 10:
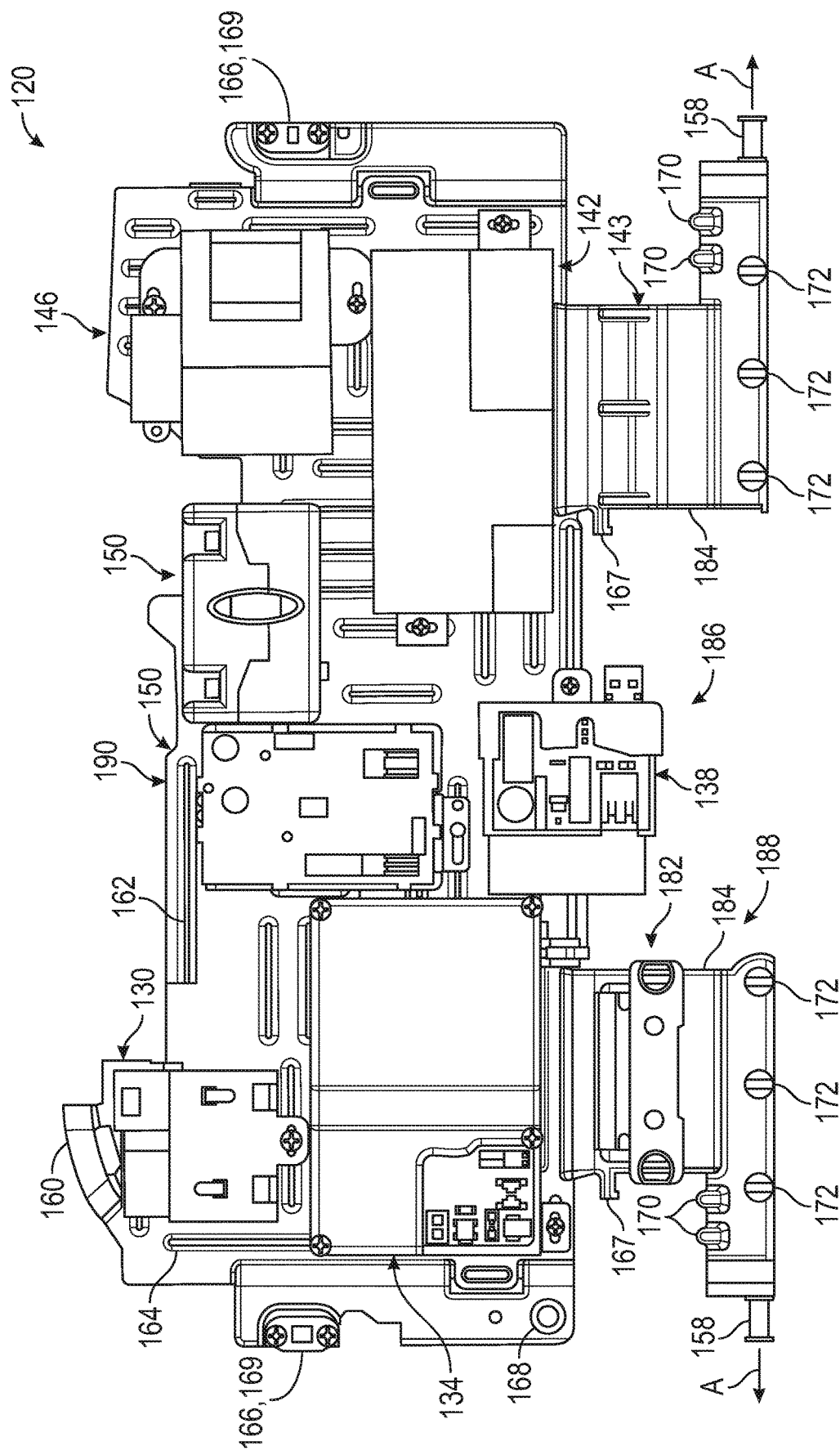
FIG. 10 is a top plan view of the shelf member of FIGS. 2-6 as fitted with various components for use.

FIG. 10 is a top plan view of the shelf 120 configured for operation with a representative arrangement of devices coupled to the shelf member 120. For example, the shelf member 120 can be fitted with devices such as a camera module 130, a hybrid air/electric motor module 134, a USB hub 138, a dual electric motor module 142, a scaler module 146, a curing light module 150 and warm water syringe module 154. These devices are shown coupled to shelf member 120, such as with screws, hook-and-loop fasteners, cable ties or other fasteners, at adjustable locations among the various slots 162, 164. The various tubing, cables and other connections for these devices have been omitted for clarity, but in general each device would have one or more connections to a respective handpiece positioned in one of the handpiece positions 110.

In addition, there is an electrical connector 182, such as a WAGO® connector, and a retaining clip 184 positioned on a left side. At a corresponding location on a right side, a clearance 143 for connectors (not shown) of the dual electric motor module 142 is provided.

Figure 11:
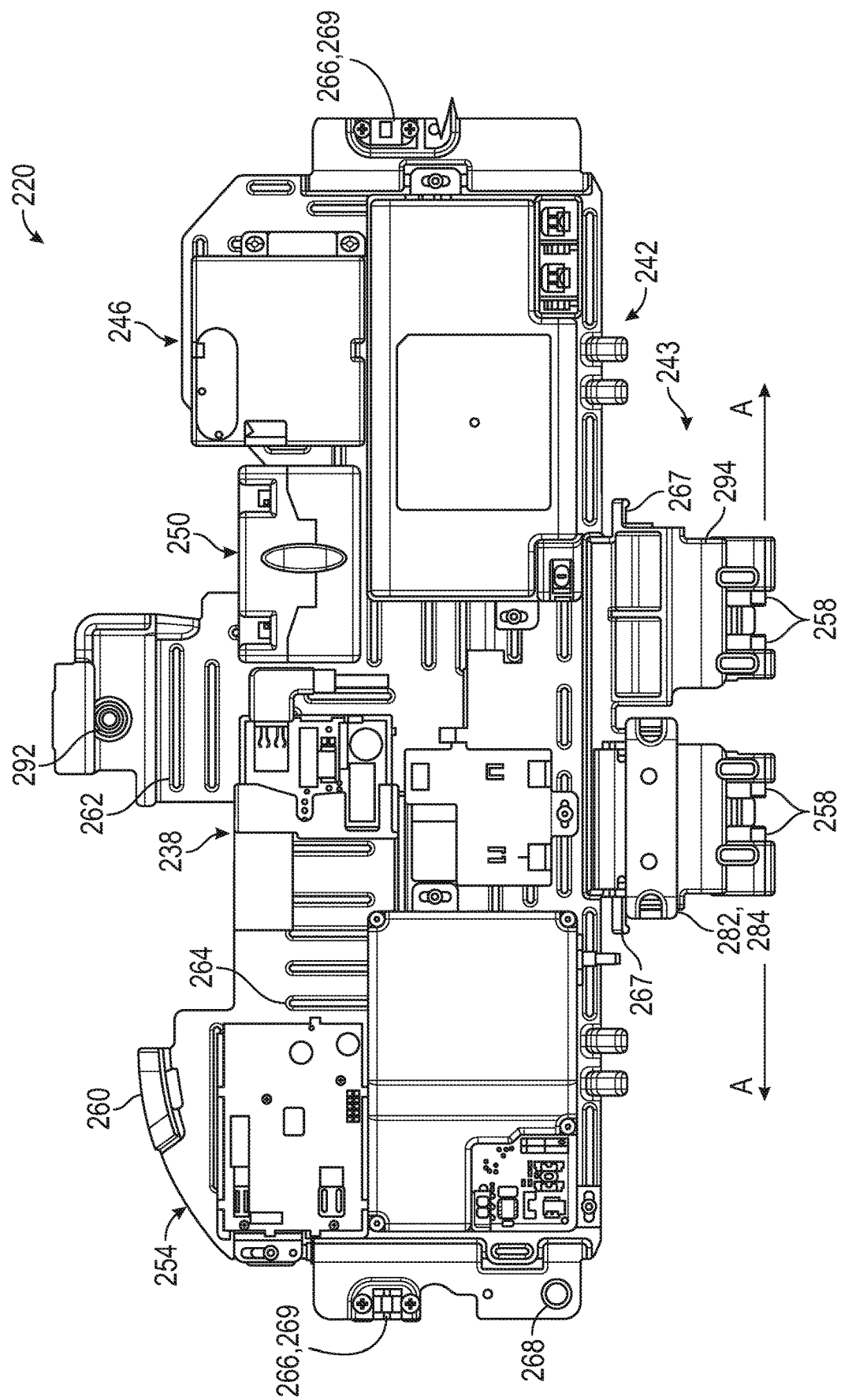
FIG. 11 is a top plan view of the shelf member of FIGS. 7-9 as fitted with various components for use.
Figure 12:
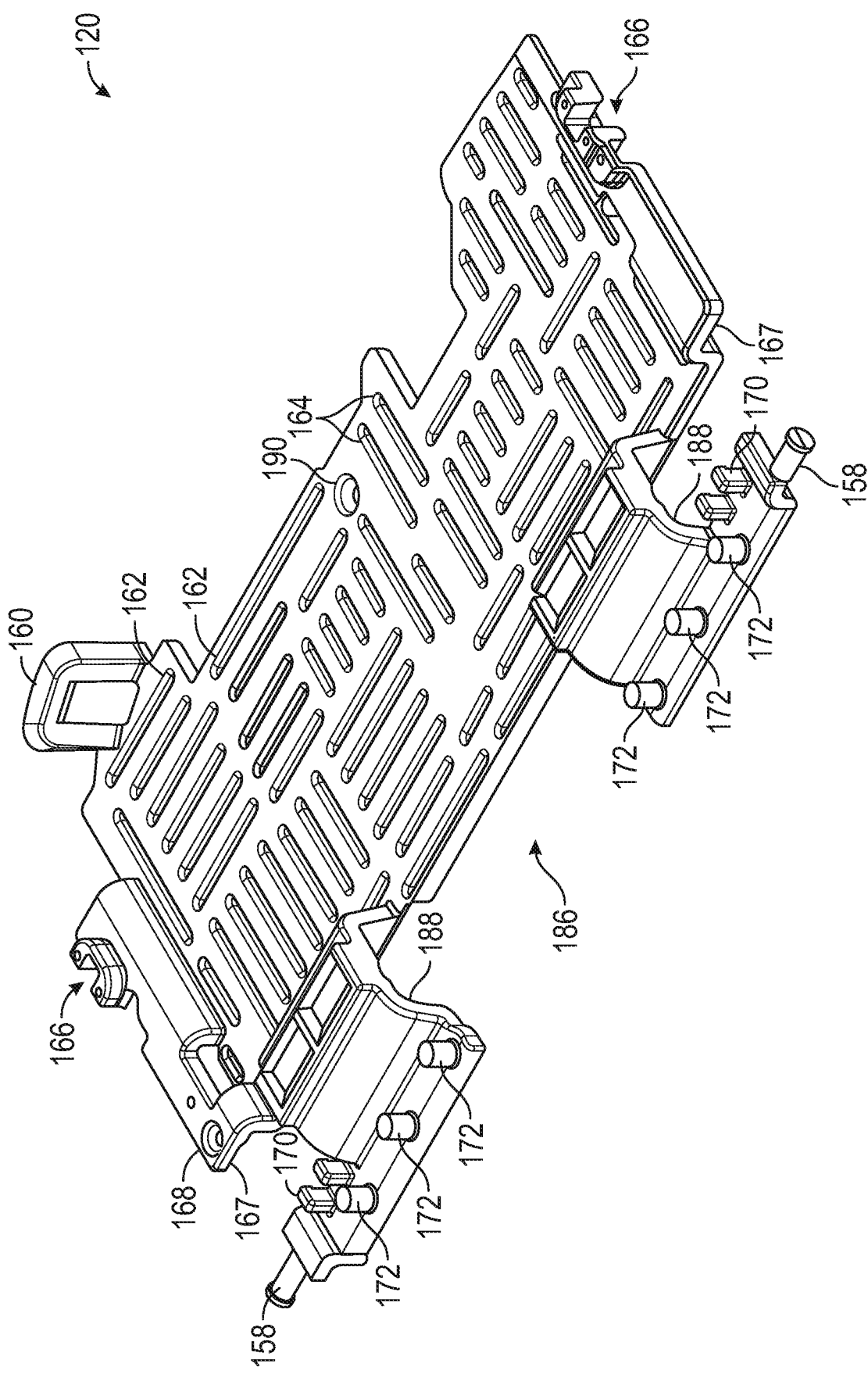
FIGS. 12-15 are perspective, top plan, bottom plan and front elevation views, respectively of the shelf member of FIG. 10 shown in isolation.
Figure 13:
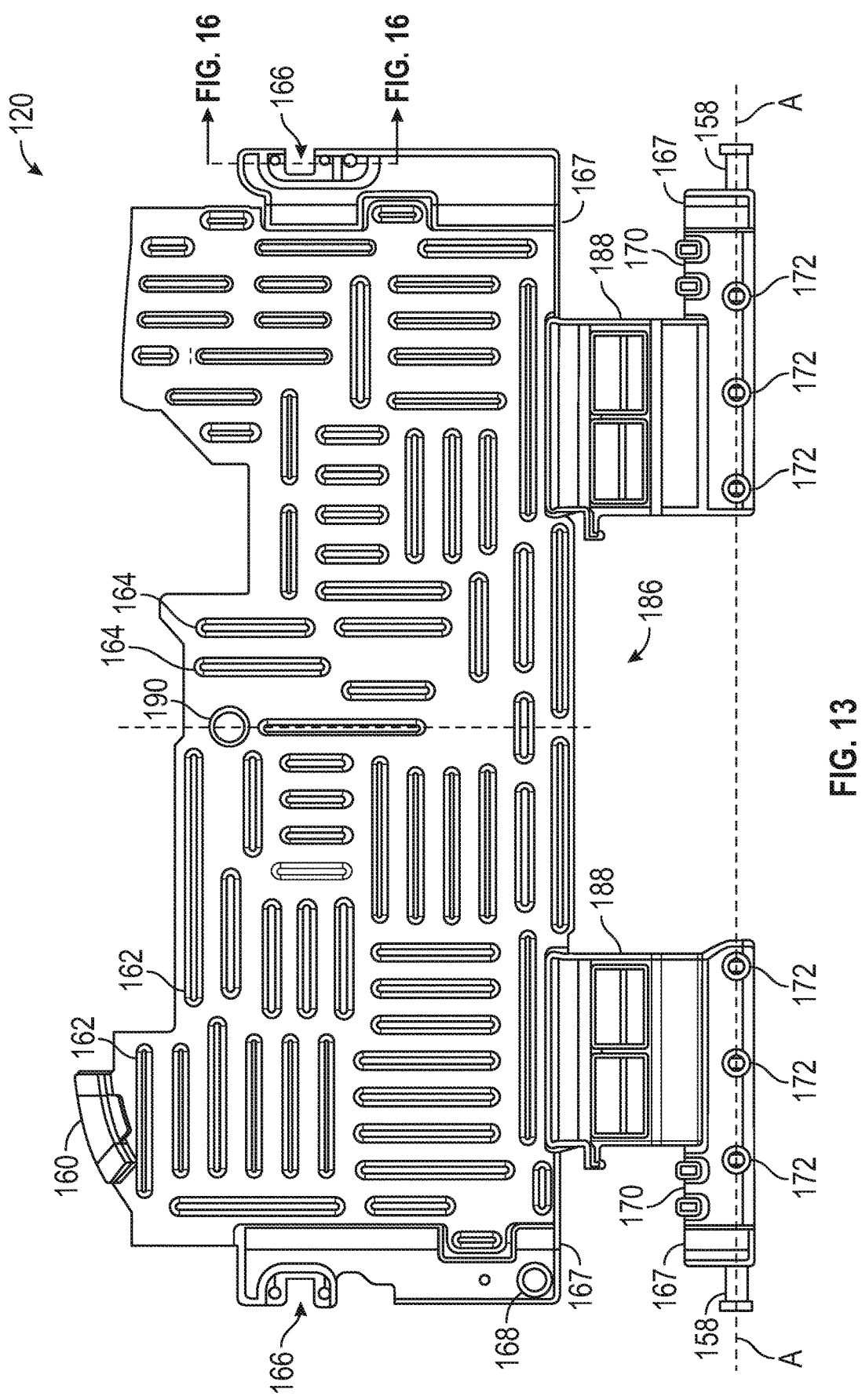
Figure 14:
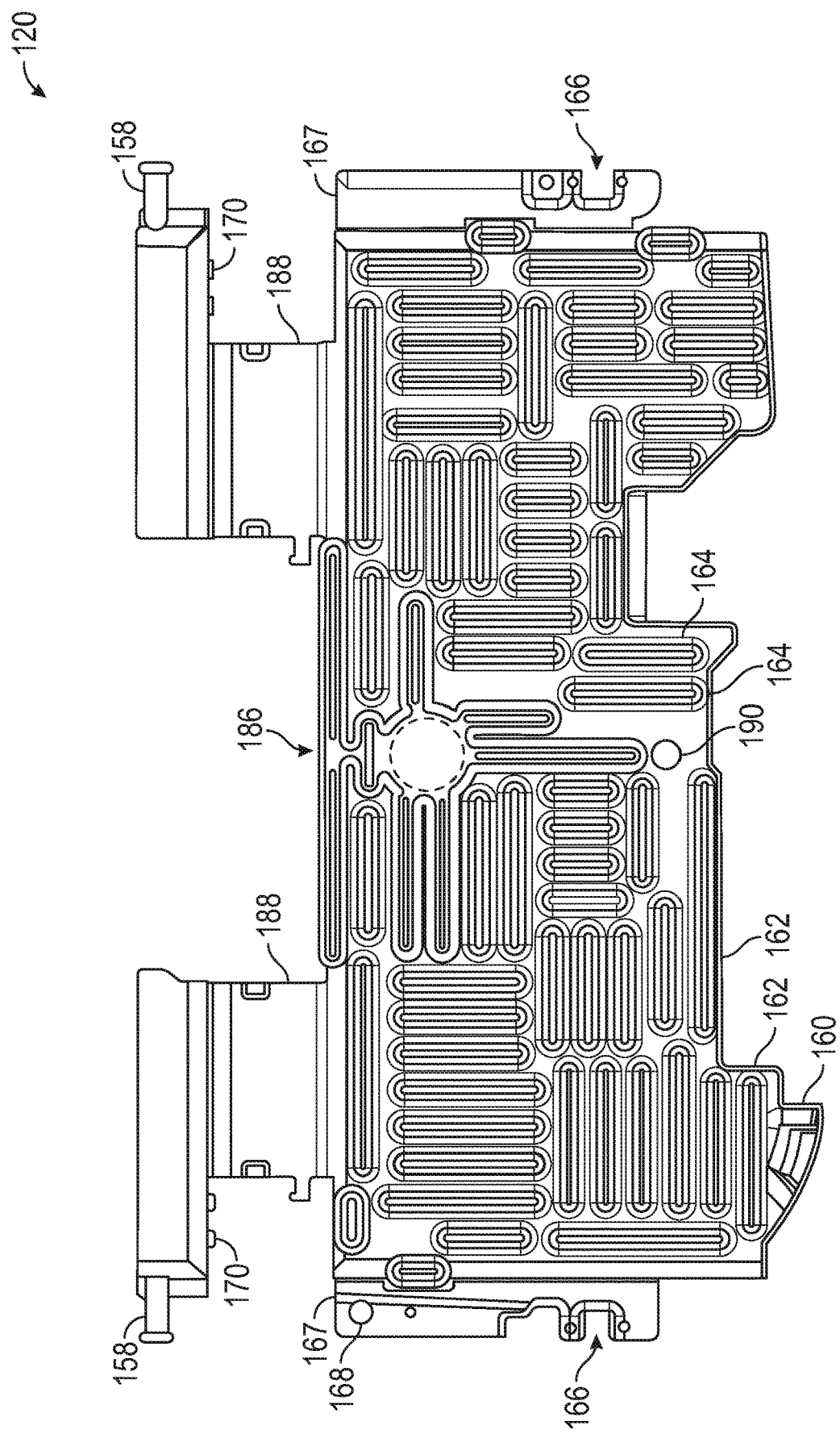
Figure 15:
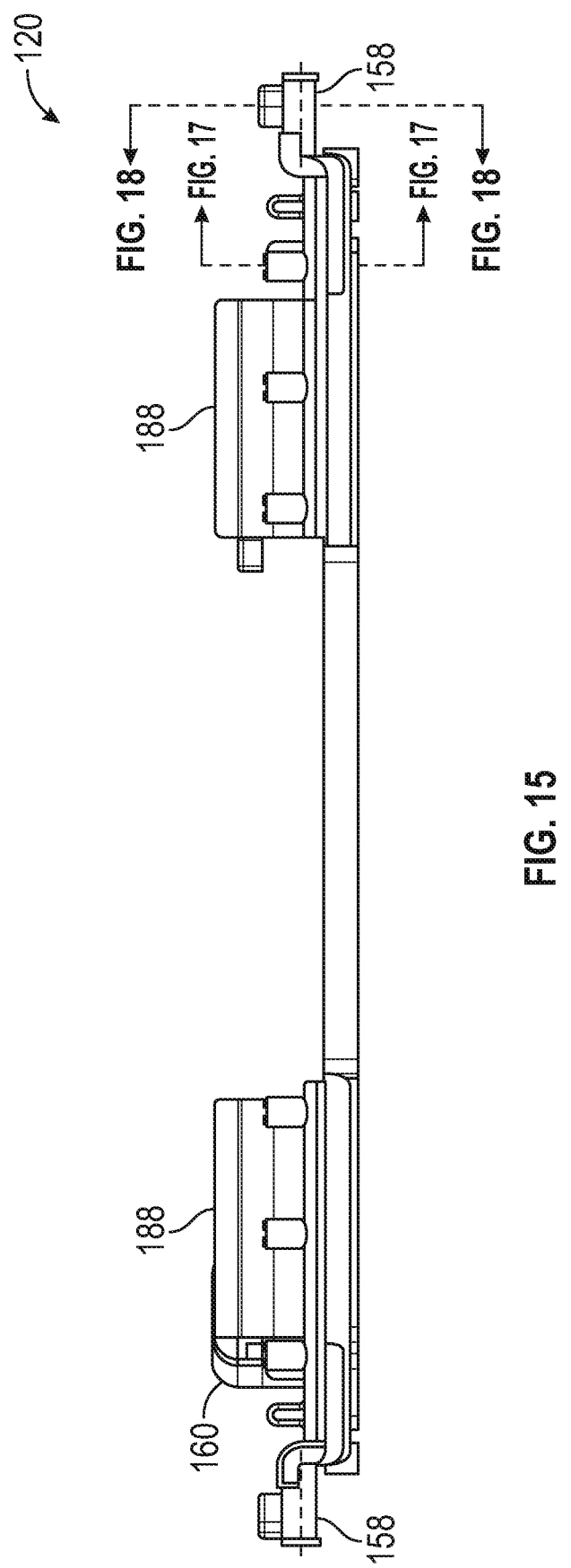

FIG. 11 is a plan view of the shelf member 220 with a representative arrangement of devices. FIG. 11 is generally similar to FIG. 10, and shows a camera module 230, a hybrid air/electric motor module 234, a USB hub 238, a dual electric motor module 242, a scaler module 246 (of a different specific type than the scaler module 146) and a curing light module 150. There is also an electrical connector 282 and clip 284. The shelf member 220 can have one or more stop surfaces, such as the angled stop surface 294 designed for coupling with a corresponding member on the cover 204 to retain the cover in the closed position.

FIG. 22 is a section view taken at the line A-A in FIG. 19 and showing the structure of the shelf 220 in the retaining device area 266 in more detail. FIG. 23 is a section view taken along the line B-B in FIG. 19 and showing the arched section 288 and the routing space it defines for one side of the shelf member 220. FIG. 24 is an enlarged detail view of the area C in FIG. 20 showing the pivots 258.

In the illustrated implementations, the shelf member 120, 220 is made of a plastic, but another suitable material could also be used.

Explanation of Terms

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods.

As used in this disclosure and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In some examples, values, procedures, or apparatus may be referred to as "lowest," "best," "minimum," or the like. It will be appreciated that such descriptions are intended to indicate that a selection among many alternatives can be made, and such selections need not be better, smaller, or otherwise preferable to other selections.

In the description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

Unless otherwise indicated, all numbers expressing quantities of components, forces, moments, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under test conditions/methods familiar to those of ordinary skill in the art. When directly and explicitly distinguishing embodiments from discussed prior art, the embodiment numbers are not approximates unless the word "about" is recited. Furthermore, not all alternatives recited herein are equivalents.

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims. We therefore claim all that comes within the scope and spirit of these claims.

We claim:

1. A dental delivery system, comprising:
a housing comprising a cover forming at least part of an upper surface of the housing, wherein the housing defines an interior and the cover is movable between a closed position enclosing the interior and an open position allowing access to the interior;
an external dental handpiece holding area positioned on the housing and separated from the interior, the external dental handpiece holding area having multiple handpiece holding spaces configured to receive dental handpieces, wherein the multiple handpiece holding spaces remain accessible while the cover is in the closed position;
at least one connection extending from the interior of the housing to one of the handpiece holding spaces of the external dental handpiece holding area, the connection being connectable to one of the dental handpieces; and
a shelf member sized to fit within the interior and being movable between at least open and closed positions while the cover is in the open position.

2. The dental delivery system of claim 1, wherein the shelf member further comprises at least one arched area projecting outwardly and defining an internal routing space for cables or tubing.

3. The dental delivery system of claim 1, wherein the shelf member comprises at least one arched area projecting outwardly and defining a recess therein through which an equipment arm can extend.

4. The dental delivery system of claim 1, wherein the shelf member comprises a lift tab by which the shelf member can be moved between the open and the closed position.

5. The dental delivery system of claim 4, wherein the shelf member comprises multiple mounting positions at which at least one of a camera module, a hybrid air/electric motor module, a Universal Serial Bus (USB) hub, a dual electric motor module, a scaler module or a curing light module can be secured.

6. The dental delivery system of claim 5, wherein the multiple mounting positions comprise slots formed in the shelf member.

7. The dental delivery system of claim 5, further comprising a first dental handpiece and a first device comprising at least one of a camera module, a hybrid air/electric motor module, a Universal Serial Bus (USB) hub, a dual electric motor module, a scaler module or a curing light module secured to a first of the multiple mounting positions, and wherein the first device is configured to be connected via the at least one connection to the first dental handpiece.

8. The dental delivery system of claim 1, wherein the shelf member comprises multiple strain relief mounts, each strain relief mount being configured to receive a corresponding strain relief portion of a handpiece conduit to be connected to the dental delivery system.

9. The dental delivery system of claim 1, wherein the shelf member is pivotably coupled to the housing and is pivotable between the open position and the closed position.

10. The dental delivery system of claim 1, wherein the at least one connection comprises a conduit for fluid, electrical power or data, and wherein the conduit is associated with at least one device mounted to the shelf member.

11. The dental delivery system of claim 1, wherein the cover is pivotably connected to the housing.

12. The dental delivery system of claim 1, wherein the shelf member and the housing comprise a retainer arrangement for retaining the shelf member in the closed position relative to the housing.

13. The dental delivery system of claim 1, wherein the shelf member in the closed position defines a lower area of the housing at a level below the shelf member and an upper area of the housing above the shelf member.

14. The dental delivery system of claim 13, wherein at least one conduit for fluid is routed through a lower area of the housing.

15. The dental delivery system of claim 1, wherein the cover is detachably removable from the housing.

16. The dental delivery system of claim 1, wherein the cover is pivotably attached to the housing, and wherein when the cover is in the closed position, the external dental handpiece holding area is at a level below the cover.

17. The dental delivery system of claim 16, wherein the external dental handpiece holding area is positioned along at least one side of the housing, and wherein the shelf member is pivotable in a direction toward the external dental handpiece holding area to move the shelf member to the open position.

18. The dental delivery system of claim 1, wherein the external dental handpiece holding area comprises multiple whip arms positioned above the cover and the interior, the cover is pivotably connected to the housing, and the whip arms are pivotable with the cover when the cover is moved between the closed position and the open position.

19. The dental delivery system of claim 1, wherein the shelf member comprises channel portions sized to receive at least one electrical cord or tubing.

20. The dental delivery system of claim 1, wherein the cover forms at least part of opposing side surfaces of the housing.

21. The dental delivery system of claim 1, wherein the cover forms at least part of opposing front and rear surfaces of the housing.

22. The dental delivery system of claim 1, wherein the housing is configured to be supported from below by a movable arm.

* * * * *